(12) United States Patent
Min et al.

(10) Patent No.: US 7,708,710 B2
(45) Date of Patent: May 4, 2010

(54) METHOD AND APPARATUS FOR COLLECTING AND PROCESSING BLOOD

(75) Inventors: Kyungyoon Min, Gurnee, IL (US); Richard I. Brown, Northbrook, IL (US)

(73) Assignee: Fenwal, Inc., Lake Zurich, IL (US)

(*) Notice: Subject to any disclaimer, the term of this patent is extended or adjusted under 35 U.S.C. 154(b) by 407 days.

(21) Appl. No.: 10/826,420

(22) Filed: Apr. 16, 2004

(65) Prior Publication Data

US 2005/0137516 A1 Jun. 23, 2005

Related U.S. Application Data

(60) Provisional application No. 60/532,310, filed on Dec. 23, 2003.

(51) Int. Cl.
*A61M 37/00* (2006.01)
*C02F 1/44* (2006.01)
*B01D 33/15* (2006.01)

(52) U.S. Cl. .............. 604/6.01; 604/4.01; 604/5.01; 604/6.02; 604/6.03; 604/6.04; 604/6.05; 604/6.06; 604/6.07; 604/6.15; 210/645; 210/781; 210/782

(58) Field of Classification Search .............. 604/4.01, 604/5.01, 6.01–6.07, 6.1, 6.11, 6.15, 6.16, 604/7; 422/44; 210/739–741, 767, 929, 210/780–782, 787–790; 494/1, 7, 37, 31–34, 494/43–45
See application file for complete search history.

(56) References Cited

U.S. PATENT DOCUMENTS

| | | | |
|---|---|---|---|
| 3,244,363 A | 4/1966 | Hein | |
| 3,489,145 A | 1/1970 | Judson et al. | |
| 4,402,680 A * | 9/1983 | Schoendorfer | ............... 494/3 |
| 4,596,657 A | 6/1986 | Wisdom et al. | |
| 4,806,252 A | 2/1989 | Brown et al. | |
| 4,834,890 A | 5/1989 | Brown et al. | |
| 4,964,976 A * | 10/1990 | Lysaght et al. | ............... 210/650 |
| 4,985,153 A * | 1/1991 | Kuroda et al. | ............... 210/782 |

(Continued)

FOREIGN PATENT DOCUMENTS

EP 0349188 1/1990

(Continued)

OTHER PUBLICATIONS

PCT Search Report, Feb. 25, 2005.

*Primary Examiner*—Leslie R Deak
(74) *Attorney, Agent, or Firm*—Cook Alex Ltd.

(57) ABSTRACT

Methods are disclosed for collecting and separating whole blood into one or more components. A disposable blood separation fluid circuit is provided which is adapted to cooperate with a reusable separation controller. The fluid circuit includes a fluid flow path for communication with a blood source and at least one container in fluid communication with the fluid flow path. The fluid flow path is connected to a blood source and quantities of whole blood are collected in the container and one other location within the fluid circuit. The source is then disconnected from the disposable fluid circuit. The quantities of whole blood are centrifugally processed, with processing of at least a portion of one of the quantities beginning after the source is disconnected from the fluid circuit.

20 Claims, 4 Drawing Sheets

U.S. PATENT DOCUMENTS

| | | |
|---|---|---|
| 5,076,911 A | 12/1991 | Brown et al. |
| 5,523,004 A * | 6/1996 | Tanokura et al. ............ 210/782 |
| 5,651,766 A | 7/1997 | Kingsley et al. |
| 5,656,887 A * | 8/1997 | Voshell et al. ............... 313/496 |
| 5,733,253 A | 3/1998 | Headley et al. |
| 6,027,657 A | 2/2000 | Min et al. |
| 6,251,284 B1 | 6/2001 | Bischof et al. |
| 6,471,855 B1 | 10/2002 | Odak et al. |
| 6,632,191 B1 * | 10/2003 | Headley et al. ............ 604/6.01 |
| 6,695,803 B1 * | 2/2004 | Robinson et al. ........... 604/4.01 |
| 6,743,192 B1 * | 6/2004 | Sakota et al. ............... 604/6.01 |
| 7,033,512 B2 * | 4/2006 | Hlavinka et al. ............ 210/787 |
| 2002/0011452 A1 | 1/2002 | Mari et al. |
| 2002/0128583 A1 | 9/2002 | Min et al. |

FOREIGN PATENT DOCUMENTS

| | | |
|---|---|---|
| WO | WO 03/078963 A2 | 9/2003 |

* cited by examiner

METHOD AND APPARATUS FOR COLLECTING AND PROCESSING BLOOD

BACKGROUND OF THE INVENTION

This application hereby claims priority to and benefit of U.S. Provisional Patent Application Ser. No. 60/532,310, filed Dec. 23, 2003, which is hereby incorporated by reference.

The present invention relates to methods for collecting and separating whole blood into one or more components.

It is well known to collect whole blood from healthy donors for subsequent administration to patients that need one or more blood components. Because patients will often require only certain blood components, it is now common to separate whole blood collected from healthy donors into one or more components (commonly called "apheresis"), such as red cells, platelets or plasma. The blood components not immediately required may be stored or processed further for other applications, or the unneeded components may be returned to the donor. Apheresis may also be employed as a therapeutic procedure for removing one or more blood components from an ill patient.

Blood processing or apheresis devices currently available for carrying out such blood collection processes include the CS-3000®, Amicus®, Autopheresis-C® and Alyx® blood separation devices marketed by Baxter Healthcare Corporation of Deerfield, Ill. Apheresis devices available from other manufacturers include the Spectra® and Trima® from Gambro BCT of Lakewood, Colo., the AS104 ™ from Fresenius Hemocare, Inc. of Redmond, Wash. and the V-50 ™ and other models from Haemonetics Corporation of Braintree, Mass. These devices typically employ a pre-assembled sterile fluid flow circuit that is disposable, and an associated reusable controller or control module that controls processing through the fluid circuit.

In the above-identified devices the donor or other human subject typically remains attached to the device throughout an entire blood collection procedure, which may be as little as 20-25 minutes or as long as 90 minutes or thereabouts. However long it takes, a separate blood processing controller or control module device is usually associated with each human subject (donor or patient), and the subject remains connected to the fluid circuit throughout the entire processing.

Although specialized devices have been proposed for collecting blood from a donor and processing it after the donor is disconnected, see, e.g. U.S. Pat. No. 4,806,252, to Brown et al., there is a continuing desire to develop versatile blood collection apparatus and methods in order to improve the efficiency of device usage, to reduce costs and to minimize imposition upon donor time and reduce inconvenience.

SUMMARY OF THE PRESENT INVENTION

In accordance with the present invention, methods are provided for collecting and separating whole blood into one or more components with improved efficiency and reduced inconvenience. According to one aspect, a method includes providing a disposable blood separation fluid circuit which is adapted to cooperate with a reusable separation controller or control module that is also suitable for other blood separation applications and processes. The fluid circuit includes a fluid flow path for communication with a blood source, such as a blood vessel of a human subject, donor or patient, and a first container in fluid communication with the flow path and a second container in fluid communication with the first container and the flow path.

In accordance with the method of the present invention, the fluid flow path is connected to a blood source, such as a healthy human donor, although the method of the present invention is not limited to collecting and separating whole blood from humans in general or from healthy donors in particular. Quantities of whole blood are flowed into the containers. The fluid circuit is then disconnected from the source. In the case of a healthy donor, the donor may then leave the blood collection site or center and the donor's presence and time are no longer required.

At least a portion of the quantity of whole blood collected in the first container is centrifugally processed through the disposable fluid circuit assembly to separate it into the desired components for removal of at least a portion of one of the components from the first container. Centrifugal processing of at least a portion of the other quanity of whole blood is begun after the source is disconnected from the fluid circuit.

In accordance with other aspects of the present invention, a method includes providing a disposable blood separation fluid circuit which is adapted to cooperate with a reusable separation controller or control module that is also suitable for other blood separation applications and processes. The fluid circuit includes a fluid flow path for communication with a blood source and a container in fluid communication with the flow path. The flow path is connected to the source and quantities of whole blood are flowed from the source into the fluid circuit and the container. The source is then disconnected from the fluid circuit. At least a portion of the quantity of whole blood collected in the container is centrifugally processed to separate it into the desired components for removal of at least a portion of one of the components from the container. Centrifugal processing of at least a portion of the quantity of whole blood in the fluid circuit is begun after the source is disconnected from the fluid circuit.

In accordance with a further aspect of the present invention, a method includes providing a disposable blood separation fluid circuit which is adapted to cooperate with a reusable separation controller or control module that is also suitable for other blood separation applications and processes. The fluid circuit includes a fluid flow path for communication with a blood source, and a container in fluid communication with the flow path, and a blood processing chamber in fluid communication with the container and the flow path. The flow path is connected to the source and quantities of whole blood are flowed from the source into the blood processing chamber and the container. The source is then disconnected from the fluid circuit. At least a portion of the quantity of whole blood collected in the blood processing chamber is centrifugally processed to separate it into the desired components for removal of at least a portion of one of the components from the blood processing chamber. Centrifugal processing of at least a portion of the other quantity of whole blood is begun after the source is disconnected from the fluid circuit.

The present invention is described herein in the context of the Fenwal Alyx® Blood Collection and Separation System. The present invention is not, however, limited to a particular system or to a system made by a particular manufacturer. It may be employed in connection with or using other blood collection and separation systems now available or that may yet be developed and used for a variety of blood processing procedures.

Although described in terms of the Alyx® Blood Collection System marketed by Fenwal, Inc., the present invention may find application, as noted above, in other blood collection systems and devices without departing from the present invention, which is defined in the attached claims.

BRIEF DESCRIPTION OF THE FIGURE OF THE DRAWINGS

DETAILED DESCRIPTION

The present invention is described herein in the context of the Baxter Alyx® Blood Collection and Separation System. The present invention is not, however, limited to a particular system or to a system made by a particular manufacturer. It may be employed in connection with or using other blood collection and separation systems now available or that may yet be developed and used for a variety of blood processing procedures.

Figure 1:
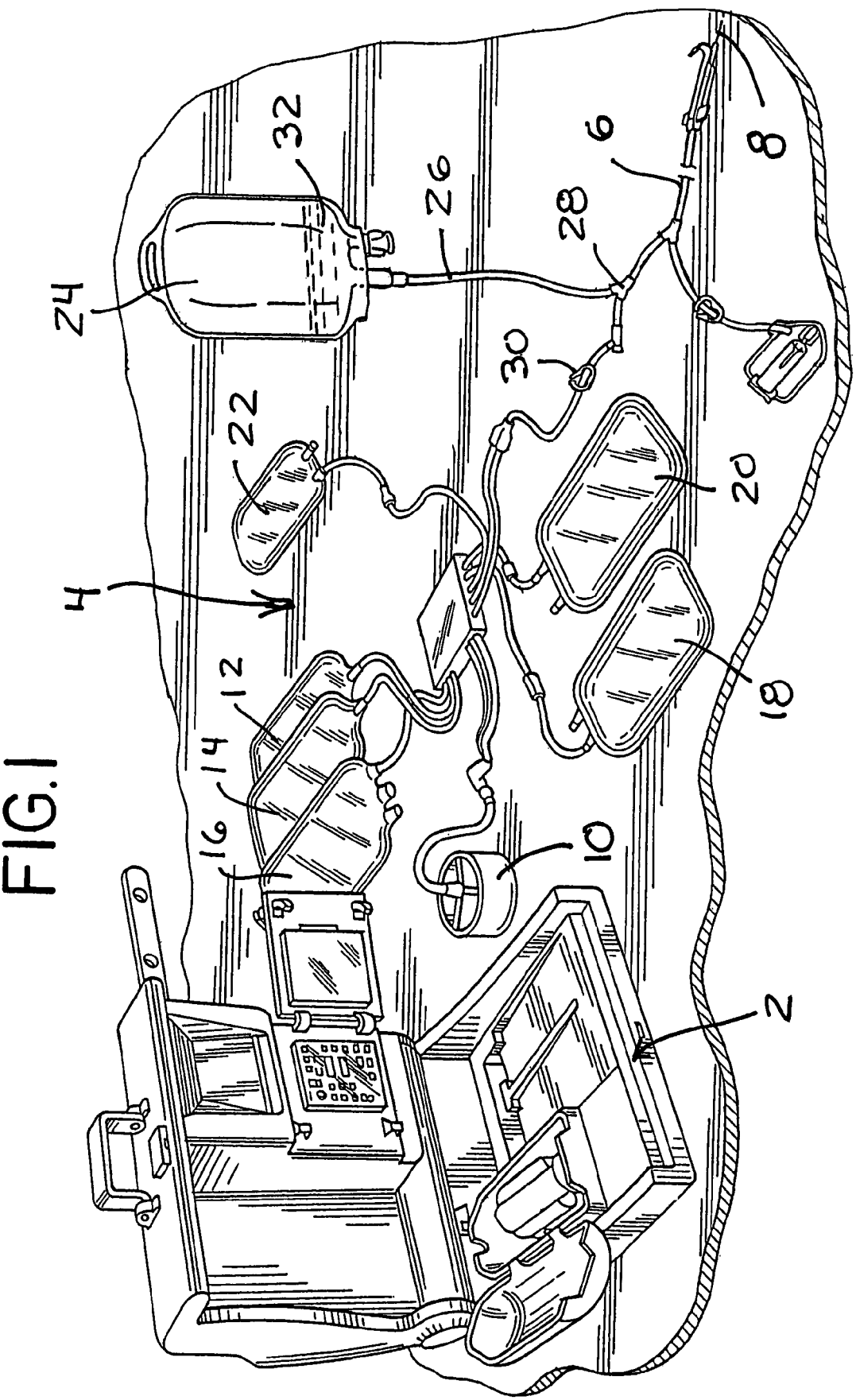
FIG. 1 is a perspective view of a reusable blood separation controller or control module and disposable fluid circuit assembly of the type embodied in and which may be employed in connection with the present invention, before the fluid circuit assembly is mounted on the controller.

As shown in FIG. 1, the system includes a reusable controller or control module 2 for carrying out a blood separation process in cooperation with a pre-sterilized and preferably, but not necessarily, integral, pre-assembled and disposable fluid circuit assembly, generally at 4. The reusable controller or control module and disposable circuit assembly are described in greater detail in one or more of the following patents or patent applications, each of which is hereby incorporated by reference into this description: U.S. Pat. No. 6,325,775 and PCT Applications Nos. PCT/US02/31317; PCT/US02/31319; PCT/US03/33311 and PCT/US03/07944.

As noted earlier, the present invention may also be employed with other apheresis systems, such as the Amicus® separator (shown in U.S. Pat. No. 5,370,802), the Autopheresis C® separator (shown in U.S. Pat. Nos. 5,135,667 and 5,194,145), the Haemonetics V-50 ™ separator, the Gambro Spectra® and Trima® separators and others as mentioned earlier. Each of the U.S. patents mentioned in this paragraph are hereby incorporated by reference herein.

As seen in FIG. 1, the disposable fluid circuit assembly 4 includes a fluid path, generally at 6, in the form of flexible plastic tubing terminating in a needle 8 for accessing a blood source, such as a blood vessel of a human subject. In the typical application, the blood source will be a human subject and more typically will be a healthy donor contributing blood or blood components for later administration to a patient. However, unless specified in the claims, the present invention is not limited to use with a particular whole blood source or to a healthy donor. The fluid flow path continues from the needle, through the fluid circuit and into other, downstream components of the fluid circuit, such as processing chambers 10 and bags 12-22 for processing in order to separate the collected blood into one or more blood components, such as red cells, platelets, and plasma.

Figure 2:
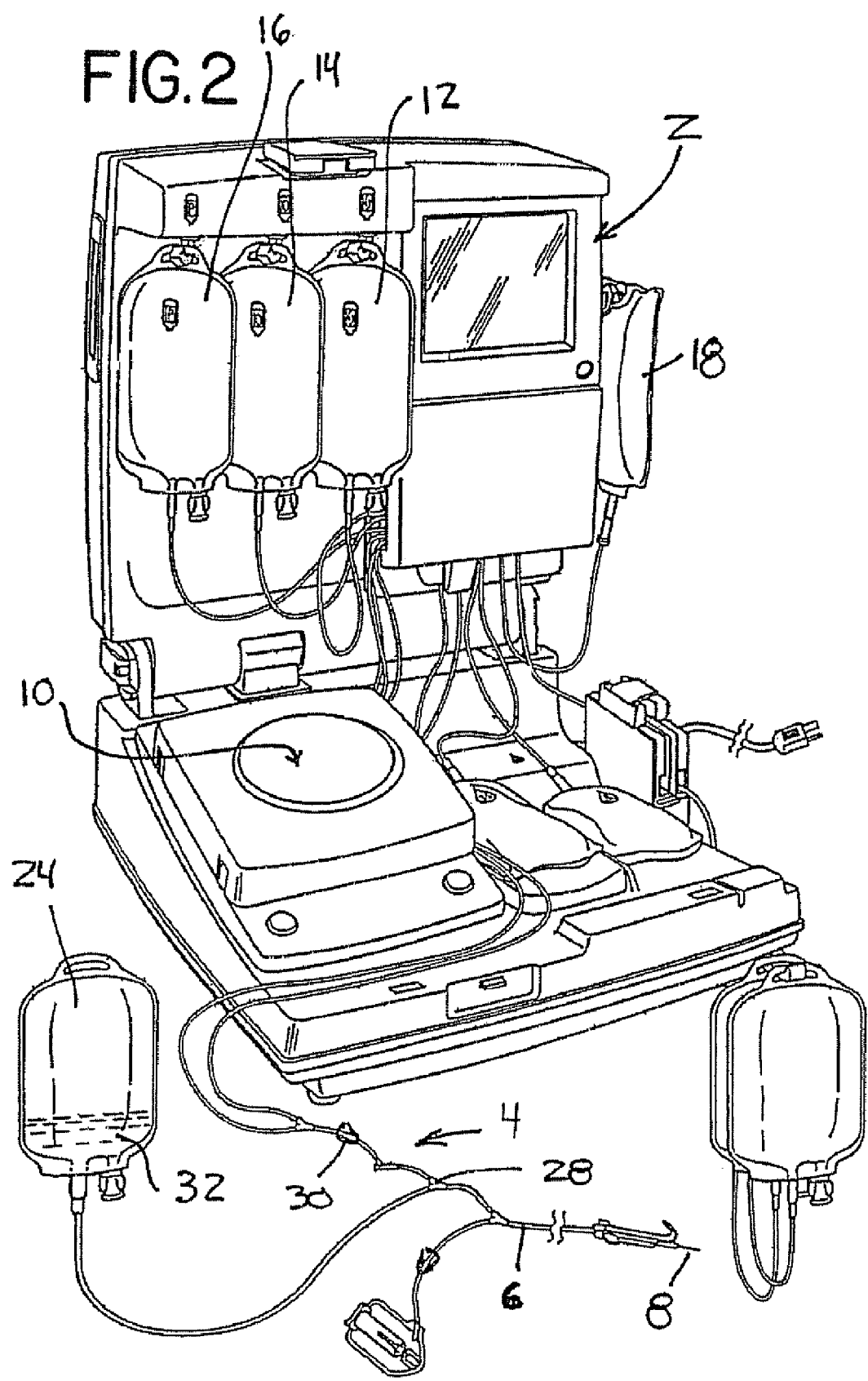
FIG. 2 is a perspective view of the apparatus of FIG. 1 after the fluid circuit assembly is mounted in association with the reusable controller.

The disposable fluid circuit may include an initial collection chamber 24, such as flexible plastic container or pouch, in fixed fluid communication with the flow path 6. In FIGS. 1 and 2, tubing 26, which joins with the fluid path 6 at an appropriate junction, such as a T-site, Y-site, V-site or other connector arrangement 28, extends to the initial collection container. The initial collection chamber could also be directly in-line in the fluid flow path 6 so that blood collected from the source flows directly into the initial collection chamber. The centrifugal processing chamber 10 itself also could have sufficient volume to serve as an initial collection chamber, if desired, although it may be preferred for other reasons (such as reduced extra corporeal blood volume in other procedures in which the processing chamber is used) to have a processing chamber of much smaller volume than may be desired for the present invention. If the separation chamber were to have sufficient volume, it is preferred that such chamber would be a standard chamber for the particular separation system, such as a standard Haemonetics separator, which does not require substantial modification of the controller or control module. Other connection arrangements for the initial collection chamber could, of course, be provided without departing from the present invention. It is desired that a collection volume be provided to collect an initial quantity of blood directly from the source before significant processing takes place, and the particular construction of such collection chamber, whether it be a separate initial collection container, separation chamber or some other structure defining the initial collection chamber, is within the scope of the present invention.

In accordance with the present invention, the disposable fluid circuit assembly 4 may, in the case of a human blood source, be connected by introduction of the needle 8 into the subject's blood vessel, typically a blood vein, as used in normal blood collection or apheresis procedures. The fluid circuit assembly may be already mounted on the controller or control module 2 at the time of connection to the human subject. It may be more cost effective, however, if the disposable fluid circuit assembly is not mounted on the reusable controller or control module at the time of attachment to the source or during subsequent collection of blood from the source.

In a manner well known and understood, whole blood may be collected from the human subject and allowed to flow into the initial collection chamber. In the situation where the chamber 10 is a separate bag or pouch as shown in FIG. 1, blood flow may be diverted into the chamber by closing clamp 30 on the fluid flow path downstream of the connection site 28 for the tubing 26.

Whole blood received within the initial collection chamber is also preferably mixed with anticoagulant 32 contained in the initial collection chamber to prevent coagulation or blood clotting. Of course, anticoagulant could be added from a separate container and metered into the blood as it is drawn from the subject if desired. It is anticipated that it will be more convenient for the user or collecting agency to have a quantity of anticoagulant already contained within the initial collection chamber for immediate mixing with the blood as collected from the human subject.

As noted earlier, where the blood source is a human donor, it is expected that typically a "unit" of blood will be initially collected—a unit being as defined in accordance with the rules or practices of the particular agency involved in the collection, or as may be defined by any appropriate government or health agency or regulation. It is anticipated that typically from about 200 to about 750 ml of whole blood will be collected in the initial collection chamber and preferably 405-550 ml and more commonly about 500 ml of whole blood will be initially collected, although the exact volume or range of volumes may vary as between different collecting organizations and/or in different countries or regions of the world.

After the desired quantity of whole blood is collected into the initial collection chamber, the blood source (donor or patient) may be disconnected from the fluid flow path. Since the presence of the source is no longer required, a donor does not need to remain attached to the set while further blood processing or separation occurs, and may leave the collection site and go about his or her business as desired. Accordingly, the only time required for a human subject in this blood collection process is the time required for initial screening, connecting and draining, e.g., by gravity, into the initial collection chamber. It is contemplated that a healthy donor will be attached to the fluid circuit approximately 7-10 minutes, which significantly reduces and minimizes the time that the human subject must devote to the collection procedure and minimizes inconvenience associated with the collection. It is well known and understood in the blood banking field that one of many obstacles to obtaining blood donors is the time commitment and the potential inconvenience to the donor in making the blood donation. Accordingly, to the extent progress can be made in reducing the amount of time required for the blood donation and reducing any perceived inconvenience to the donor it will be of potentially significant benefit in increasing and maintaining the existing pool of blood donors.

After the human subject or donor is disconnected from the fluid circuit, such as by withdrawing the needle 8, the tubing 6 may be sealed and severed from the remainder of the fluid circuit, if so desired. The fluid circuit may then, if not already installed on the reusable controller or control module, be installed thereon in order to process the blood collected in the initial collection chamber using such process as the controller may be programmed to carry out. For example, the controller may be programmed to collect human red cells and plasma containing platelets. Alternatively, the controller may be programmed to collect concentrated platelets and plasma. The blood in the initial collection chamber may be processed sequentially or simultaneously.

In any event, the whole blood may be processed through the controller in such a manner as is most convenient and efficient for the collecting agency without concern for further inconvenience to or time required of the donor or other blood source. It is also unnecessary for each donor or other blood source to have associated with them a dedicated controller or control module. For example, blood from a number of sources may be pooled together into a single flow path for subsequent processing. Accordingly, the controller may be located at the collection site where whole blood is being collected for convenient processing promptly after collection or, alternatively, the controller or control module may be at an entirely different location than where the blood is initially collected from the human subject or other blood source. As a result, one controller or control module may be used for processing blood collected from many different human subjects, thus, significantly reducing the capital cost required by blood collection centers or agencies, in comparison to those situations where it is necessary to have a reusable controller or control module associated with each donor throughout all or a significant portion of the time of collection and/or processing.

As a further possible efficiency in connection with the present invention, it may be possible to connect more than one initial collection chambers to a given fluid circuit assembly, so that blood collected from various donors may be processed through the same disposable fluid circuit assembly. This may be achieved by providing additional connection sites such as a Y connector 28 on the fluid path 6, for attachment of an initial collection chamber used to collect blood from another donor. Multiple connection sites 28 may be provided on the fluid path 6 so that a plurality of initial collection chambers could be connected for processing whole blood collected from several different donors. Instead of a connection site, one or more sealed branch tubing lengths may be provided for connection to collection chambers by a sterile connection device, allowing blood in additional collection chambers to be processed serially or in parallel through the same fluid circuit. Also, it may be possible to pool several initial collection chambers into a single container for processing through the fluid circuit assembly.

In short, the present invention provides a particularly unique and novel method and apparatus for collecting and separating whole blood into one or more components which has substantial benefit in reducing the amount of source or donor time or human subject time required for connection to the separation apparatus, reducing any potential inconvenience to the donor and increasing the efficiency of hardware usage and lowering capital requirements.

Figure 3:
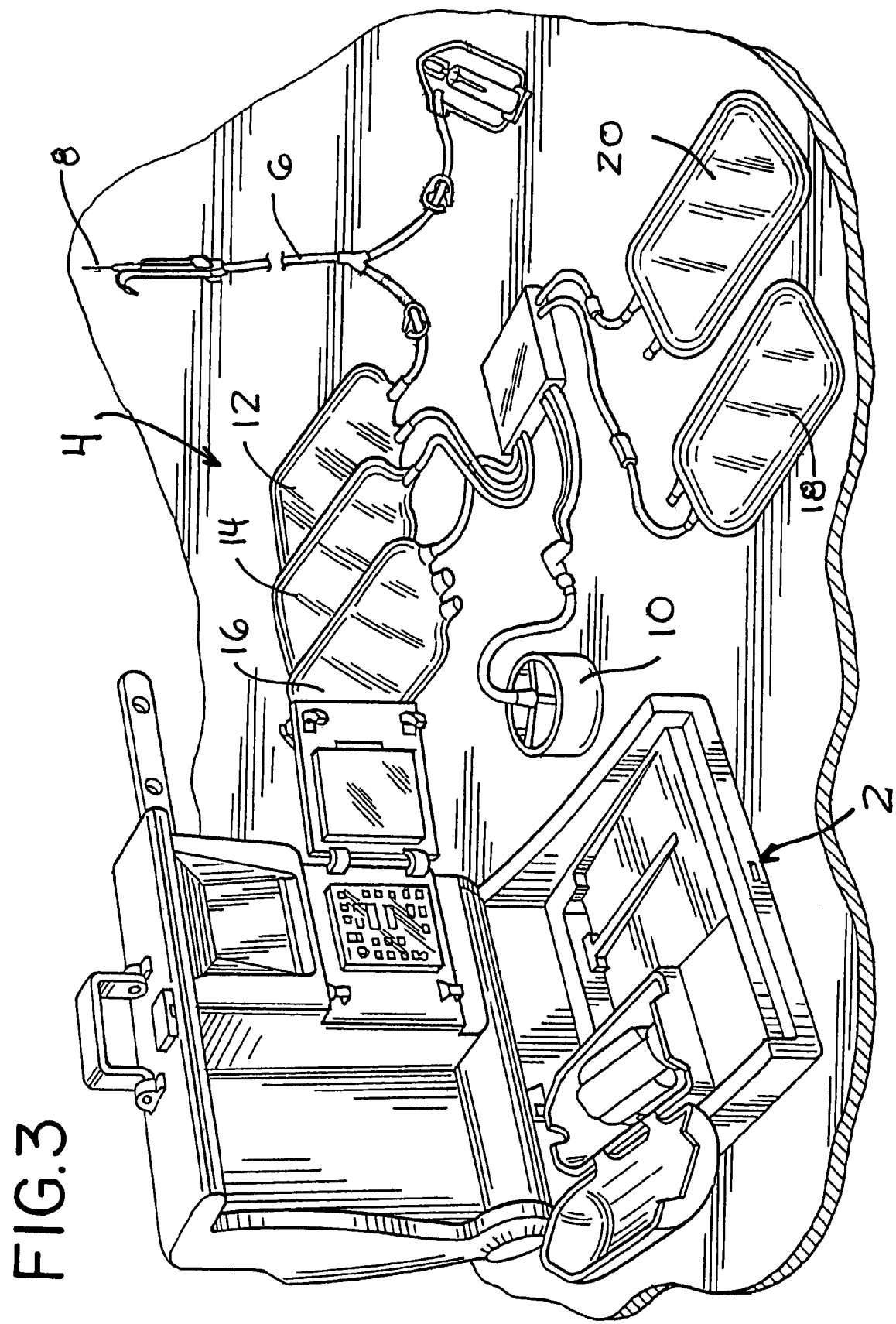
FIG. 3 is a perspective view of a reusable blood separator controller or control module and an alternate disposable fluid circuit assembly of the type embodied in and which may be employed in connection with the present invention, before the fluid circuit assembly is mounted on the controller.
Figure 4:
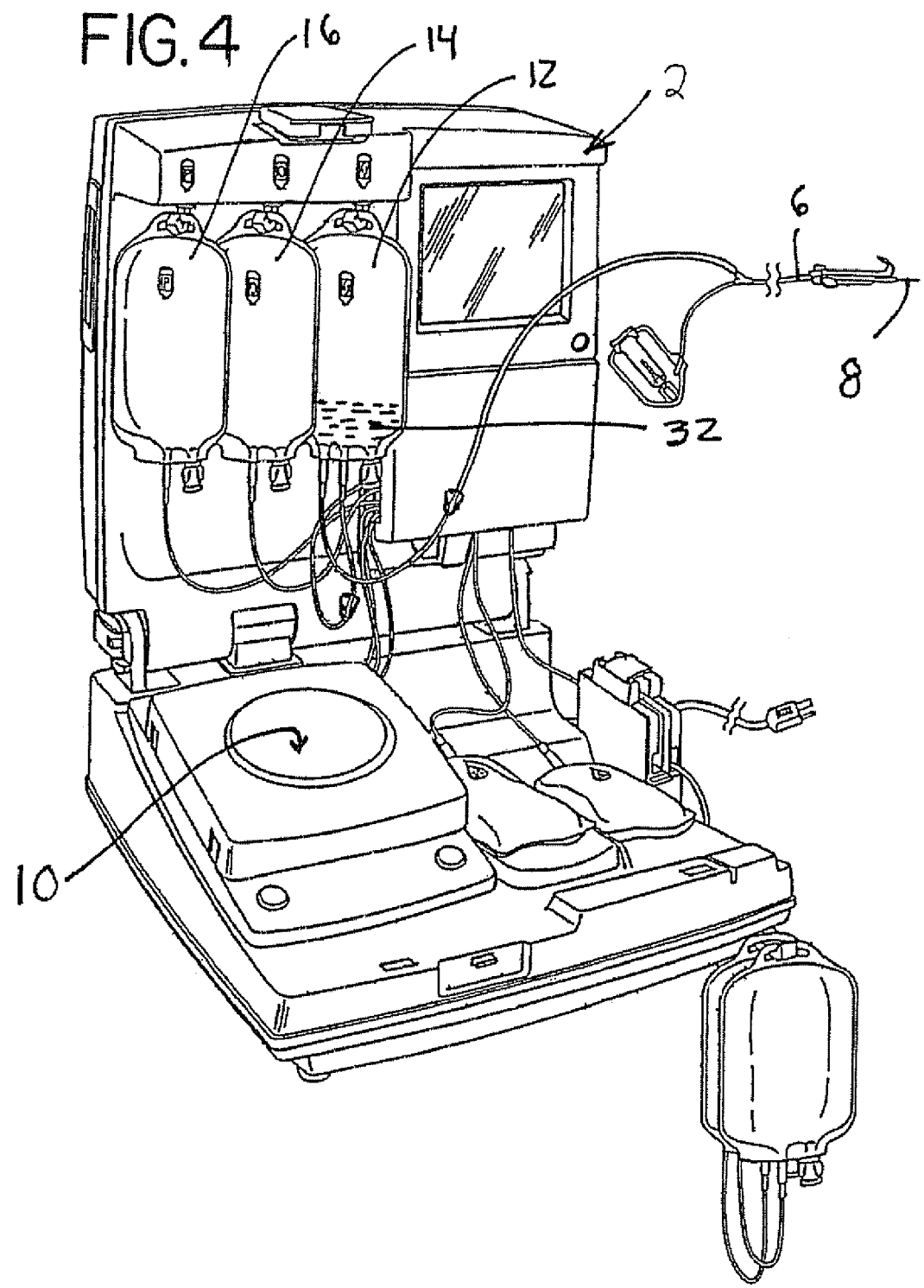
FIG. 4 is a perspective view of the apparatus of FIG. 3 after the disposable fluid circuit assembly is mounted in association with the reusable controller.

An alternative processing apparatus is shown in FIGS. 3 and 4. This embodiment differs from the FIGS. 1 and 2 version in that a pre-connected container that is part of a standard Alyx® disposable fluid circuit assembly or set is used as the initial collection container, and it is unnecessary to have a further or additional container joined to the set to function as the initial collection container. More specifically, in FIGS. 3 and 4, container or bag 12, which is commonly referred to as the "in-process" container in typical Alyx® system red cell collection procedures (described in one or more of the patents and patent applications incorporated by reference above), serves as an initial collection container for receiving the desired quantity of blood from the blood source. In such a fluid circuit arrangement, the access needle 8 may be attached, via inlet tubing 6, directly to the in-process container 12. A quantity of anticoagulant 32, such as ACD or other anticoagulant, may be pre-placed inside the in-process container or bag to mix with whole blood as it collected from the blood source. The quantity of blood collected may be automatically monitored by a scale from which the in-process container hangs, if the system is installed on the control module 2 at the time of collection. Otherwise the quantity may be visually monitored by the operator as it is in typical manual blood collection procedures.

When the desired quantity of blood is collected in the in-process container, the inlet tubing 6 may be sealed and severed to remove the needle 8. Clamp 30 (or an internal frangible flow control member) may be opened, and the collected blood may then be processed through the fluid circuit assembly to separate the whole blood and collect the desired blood components. In this arrangement and process, the anticoagulated whole blood may itself be used to prime the remainder of the fluid circuit assembly, and it may be unnecessary to have a separate container of saline as part of the pre-assembled and pre-sterilized fluid circuit assembly. Of course, because the system is disconnected from the blood source after the desired quantity of blood is collected, saline also is not required as a replacement fluid for the donor. Accordingly, the fluid circuit assembly in FIGS. 3 and 4 may be specially configured for carrying out the method of the present invention, eliminating various parts or components that are normally employed in such a disposable fluid circuit but are unnecessary or redundant for the method of the present invention.

Although described in terms of the Alyx® Blood Collection System marketed by Baxter Healthcare Corporation, the present invention may find application, as noted above, in other blood collection systems and devices without departing from the present invention, which is defined in the attached claims.

What is claimed:

1. A method for collecting and separating whole blood into one or more components comprising:
   providing a disposable blood separation fluid circuit adapted to cooperate with a reusable separation controller, the fluid circuit including a fluid flow path for communication with a blood source, a first container in fluid communication with the fluid flow path and a second container in fluid communication with the first container and the fluid flow path;
   connecting the fluid flow path to a blood source;
   flowing quantities of whole blood into said containers;
   centrifugally processing at least a portion of said quantity of whole blood in the first container to separate it into the desired components for removal of at least a portion of one of said components from the first container;
   disconnecting the source from the fluid circuit after flowing said quantities of whole blood into said containers; and
   beginning to centrifugally process at least a portion of the other of said quantities of whole blood after disconnecting the source.

2. The method of claim 1 in which at least one of the containers includes a quantity of anticoagulant.

3. The method of claim 1 in which about 200-750 ml of whole blood are flowed into the containers.

4. The method of claim 1 in which about 500 ml of whole blood are flowed into the containers.

5. The method of claim 4 in which a unit of whole blood is flowed into the containers.

6. The method of claim 1 including connecting additional collection containers of whole blood to the fluid flow path for processing through the fluid circuit.

7. The method of claim 1 in which the blood source is a human.

8. The method of claim 1 including pooling together blood from other blood sources and flowing the pooled blood into the flow path for processing through the fluid circuit.

9. The method of claim 1, wherein one of said containers is a processing chamber.

10. The method of claim 1, wherein the fluid circuit includes a clamp associated with the fluid flow path between the blood source and the containers.

11. The method of claim 1, wherein said flowing quantities of whole blood into said containers includes sequentially flowing quantities of whole blood into said containers.

12. The method of claim 1, wherein said flowing quantities of whole blood into said containers includes simultaneously flowing quantities of whole blood into said containers.

13. The method of claim 1, wherein said flowing quantities of whole blood into said containers includes flowing whole blood from one of the containers into the other container.

14. A method for collecting and separating whole blood into one or more components comprising:
   providing a disposable blood separation fluid circuit adapted to cooperate with a reusable separation controller, the fluid circuit including a fluid flow path for communication with a blood source and a container in fluid communication with the fluid flow path;
   connecting the fluid flow path to a blood source;
   flowing quantities of whole blood from the source into the fluid circuit and the container;
   centrifugally processing at least a portion of the quantity of whole blood in the container to separate it into the desired components for removal of at least a portion of one of said components from the container;
   disconnecting the source from the fluid circuit after flowing said quantities of whole blood into the fluid circuit and the container; and
   beginning to centrifugally process at least a portion of the quantity of whole blood in the fluid circuit after disconnecting the source.

15. The method of claim 14, wherein the blood from the source is collected in an initial collection container prior to processing in the container.

16. The method of claim 14, wherein said container is a processing chamber.

17. A method for collecting and separating whole blood into one or more components comprising:
   providing a disposable blood separation fluid circuit adapted to cooperate with a reusable separation controller, the fluid circuit including a fluid flow path for communication with a blood source, a container in fluid communication with the fluid flow path, and a blood processing chamber in fluid communication with the container and the fluid flow path;
   connecting the fluid flow path to a blood source;
   flowing a quantity of whole blood into the blood processing chamber;
   flowing another quantity of whole blood into the container;
   centrifugally processing at least a portion of said quantity of whole blood in the blood processing chamber to separate it into the desired components for removal of at least a portion of one of said components from the blood processing chamber;
   disconnecting the source from the fluid circuit after flowing said another quantity of whole blood into the container; and
   beginning to centrifugally process at least a portion of said another quantity of whole blood after disconnecting the source.

18. The method of claim 17, wherein said flowing a quantity of whole blood into the blood processing chamber and said flowing another quantity of whole blood into the container are performed sequentially.

19. The method of claim 17, wherein said flowing a quantity of whole blood into the blood processing chamber and said flowing another quantity of whole blood into the container are performed simultaneously.

20. The method of claim 17, wherein said flowing a quantity of whole blood into the blood processing chamber includes flowing whole blood from the container into the blood processing chamber.

* * * * *